(12) United States Patent
Bardach et al.

(10) Patent No.: US 8,978,659 B2
(45) Date of Patent: *Mar. 17, 2015

(54) THERAPEUTIC AND PROTECTIVE DENTAL DEVICE USEFUL AS AN INTRA-ORAL DELIVERY SYSTEM

(71) Applicants: Dynamic Mouth Devices, L.L.C., Boonton, NJ (US); Salvatore Napoli, Florham Park, NJ (US)

(72) Inventors: Laura Bardach, Boonton, NJ (US); James Geduldig, Boonton, NJ (US); Salvatore Napoli, Florham Park, NJ (US)

(73) Assignee: Dynamic Mouth Devices, L.L.C., Boonton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/939,825

(22) Filed: Jul. 11, 2013

(65) Prior Publication Data

US 2014/0014119 A1 Jan. 16, 2014

Related U.S. Application Data

(60) Continuation of application No. 12/001,571, filed on Dec. 12, 2007, now Pat. No. 8,505,541, which is a division of application No. 10/138,821, filed on May 6, 2002, now Pat. No. 7,328,706.

(51) Int. Cl.
*A61F 5/37* (2006.01)
*A61F 13/00* (2006.01)
(Continued)

(52) U.S. Cl.
CPC ............. *A61C 19/063* (2013.01); *A61C 19/066* (2013.01); *A63B 71/085* (2013.01); *A63B 2208/12* (2013.01)

USPC ........... 128/861; 128/846; 128/848; 128/859; 433/6; 433/37

(58) Field of Classification Search
USPC ................. 128/846, 857, 859, 861, 848, 862; 433/6, 7, 34, 37, 48, 215; 604/77, 234, 604/235; 29/896, 896.1, 896.11
See application file for complete search history.

(56) References Cited

U.S. PATENT DOCUMENTS

| 516,561 A | 3/1894 | Bosch |
| 1,298,616 A | 3/1919 | Wilson |

(Continued)

FOREIGN PATENT DOCUMENTS

AU 633269 B2 1/1993

*Primary Examiner* — Victoria J Hicks
*Assistant Examiner* — Brandon L Jackson
(74) *Attorney, Agent, or Firm* — Lerner, David, Littenberg, Krumholz & Mentlik, LLP

(57) ABSTRACT

A dental device has a U-shaped carrier with at least one channel for embracing an arch of teeth. There are recessed insets in the channel. Discrete inserts carrying a beneficial agent can fit into the insets and release the agent gradually. The device may be used in a therapeutic application and as an athletic mouthguard. Temporary blanks may be initially fitted in the insets, while a portion of the mouthguard is softened before an arch of teeth is pressed into the channel to make a custom impression. The inserts possess different physical properties than the carrier and may be positioned and shaped to mechanically buffer teeth of the arch from mechanical shocks as well as release beneficial agents. The inserts may be replaced or refreshed to maintain the beneficial agent. A dental device having a core carrying a beneficial agent inside a liquid-permeable shell functions as an infant's teething device.

25 Claims, 5 Drawing Sheets

(51) Int. Cl.
*A61C 3/00* (2006.01)
*A61C 5/00* (2006.01)
*A61C 5/14* (2006.01)
*A61C 9/00* (2006.01)
*A61B 19/00* (2006.01)
*A61C 19/06* (2006.01)
*A63B 71/08* (2006.01)

(56) References Cited

U.S. PATENT DOCUMENTS

| | | |
|---|---|---|
| 2,288,470 A | 6/1942 | Lorraine |
| 2,514,844 A | 7/1950 | Cohen |
| 2,612,165 A | 9/1952 | Szuderski |
| 2,824,561 A | 2/1958 | Mueller |
| 3,223,085 A | 12/1965 | Gores et al. |
| 3,224,442 A | 12/1965 | Stubbs |
| 3,250,272 A | 5/1966 | Greenberg |
| 3,416,527 A | 12/1968 | Hoef |
| 3,503,127 A | 3/1970 | Kasdin et al. |
| 3,505,995 A | 4/1970 | Greenberg |
| 3,532,091 A | 10/1970 | Lerman |
| 3,587,590 A | 6/1971 | Hastings |
| 3,600,807 A | 8/1971 | Sipos |
| 3,818,906 A | 6/1974 | Stubbs |
| 3,996,934 A | 12/1976 | Zaffaroni |
| 4,044,762 A | 8/1977 | Jacobs |
| 4,192,307 A | 3/1980 | Baer |
| 4,193,407 A | 3/1980 | Edmark |
| 4,327,725 A | 5/1982 | Cortese et al. |
| 4,348,381 A | 9/1982 | Gaffar et al. |
| 4,350,154 A | 9/1982 | Feldbau |
| 4,447,164 A | 5/1984 | Berndt |
| 4,554,154 A | 11/1985 | White |
| 4,569,342 A | 2/1986 | von Nostitz et al. |
| 4,681,542 A | 7/1987 | Baum |
| 4,765,324 A | 8/1988 | Lake, Jr. |
| 4,920,984 A | 5/1990 | Furumichi et al. |
| 4,944,947 A | 7/1990 | Newman |
| 5,015,628 A | 5/1991 | Reynolds |
| 5,021,053 A | 6/1991 | Barclay et al. |
| 5,052,410 A | 10/1991 | Stubbs |
| 5,071,657 A | 12/1991 | Oloff et al. |
| 5,082,007 A | 1/1992 | Adell |
| 5,085,585 A | 2/1992 | Zimble |
| 5,127,903 A | 7/1992 | Mailot et al. |
| 5,152,301 A | 10/1992 | Kittelsen et al. |
| 5,194,003 A | 3/1993 | Garay et al. |
| 5,200,194 A | 4/1993 | Edgren et al. |
| 5,252,692 A | 10/1993 | Lovy et al. |
| 5,286,490 A | 2/1994 | Grodberg |
| 5,300,089 A | 4/1994 | Sassin |
| 5,323,787 A | 6/1994 | Pratt |
| 5,339,832 A | 8/1994 | Kittelsen et al. |
| 5,346,935 A | 9/1994 | Suzuki et al. |
| 5,365,624 A | 11/1994 | Berns |
| 5,366,935 A | 11/1994 | Alim et al. |
| 5,395,392 A | 3/1995 | Suhonen |
| 5,460,527 A | 10/1995 | Kittelsen |
| 5,562,895 A | 10/1996 | Tung |
| 5,566,684 A | 10/1996 | Wagner |
| 5,620,011 A | 4/1997 | Flowers |
| 5,810,886 A | 9/1998 | Hassan |
| 5,819,744 A | 10/1998 | Stoyka, Jr. |
| 5,826,581 A | 10/1998 | Yoshida |
| 5,834,427 A | 11/1998 | Han et al. |
| 5,842,860 A | 12/1998 | Funt |
| 5,895,641 A | 4/1999 | Usen et al. |
| 5,924,422 A | 7/1999 | Gustafson |
| 5,925,372 A | 7/1999 | Berner et al. |
| 5,979,449 A | 11/1999 | Steer |
| 5,980,249 A | 11/1999 | Fontenot |
| 5,981,475 A | 11/1999 | Reynolds |
| 5,993,413 A | 11/1999 | Aaltonen et al. |
| 6,012,919 A | 1/2000 | Cross, III et al. |
| 6,036,487 A | 3/2000 | Westerman |
| 6,036,944 A | 3/2000 | Winston et al. |
| 6,068,475 A | 5/2000 | Stoyka, Jr. |
| 6,082,363 A | 7/2000 | Washburn |
| 6,126,678 A | 10/2000 | Aaltonen et al. |
| 6,203,566 B1 | 3/2001 | Alanen et al. |
| 6,209,133 B1 | 4/2001 | Hinshaw |
| 6,210,699 B1 | 4/2001 | Acharya et al. |
| 6,244,269 B1 | 6/2001 | Tyler |
| 6,269,816 B1 | 8/2001 | Rigonatti et al. |
| 6,321,752 B1 | 11/2001 | Spottiswoode et al. |
| 6,412,489 B1 | 7/2002 | Sue |
| 6,447,536 B1 | 9/2002 | Hinshaw |
| 6,494,210 B1 | 12/2002 | Mams |
| 6,505,626 B2 | 1/2003 | Kittelsen et al. |
| 6,514,176 B1 | 2/2003 | Norton |
| 6,519,781 B1 | 2/2003 | Berns |
| 6,553,996 B2 | 4/2003 | Kittelsen et al. |
| 6,575,999 B1 | 6/2003 | Rohrig |
| 6,581,604 B2 | 6/2003 | Cook |
| 6,592,860 B1 | 7/2003 | Levy et al. |
| 6,635,281 B2 | 10/2003 | Wong et al. |
| 6,660,029 B2 | 12/2003 | Vanskiver et al. |
| 6,675,806 B2 | 1/2004 | Kittelsen et al. |
| 6,691,710 B2 | 2/2004 | Kittelsen et al. |
| 6,752,824 B2 | 6/2004 | Yancy |
| 7,001,357 B2 | 2/2006 | Berry, Sr. |
| 7,118,376 B2 | 10/2006 | Jodaikin et al. |
| 7,328,706 B2 * | 2/2008 | Bardach et al. ............... 128/861 |
| 7,500,984 B2 | 3/2009 | Fuisz et al. |
| 8,181,655 B2 | 5/2012 | Bardach et al. |
| 8,505,541 B2 * | 8/2013 | Bardach et al. ............... 128/861 |
| 2003/0031630 A1 | 2/2003 | Reznick et al. |
| 2003/0176891 A1 | 9/2003 | Frederic |
| 2005/0175959 A1 | 8/2005 | Jodaikin et al. |
| 2006/0155331 A1 | 7/2006 | Bohmer |
| 2006/0185679 A1 | 8/2006 | Costigan et al. |
| 2010/0034860 A1 | 2/2010 | Bardach et al. |

* cited by examiner

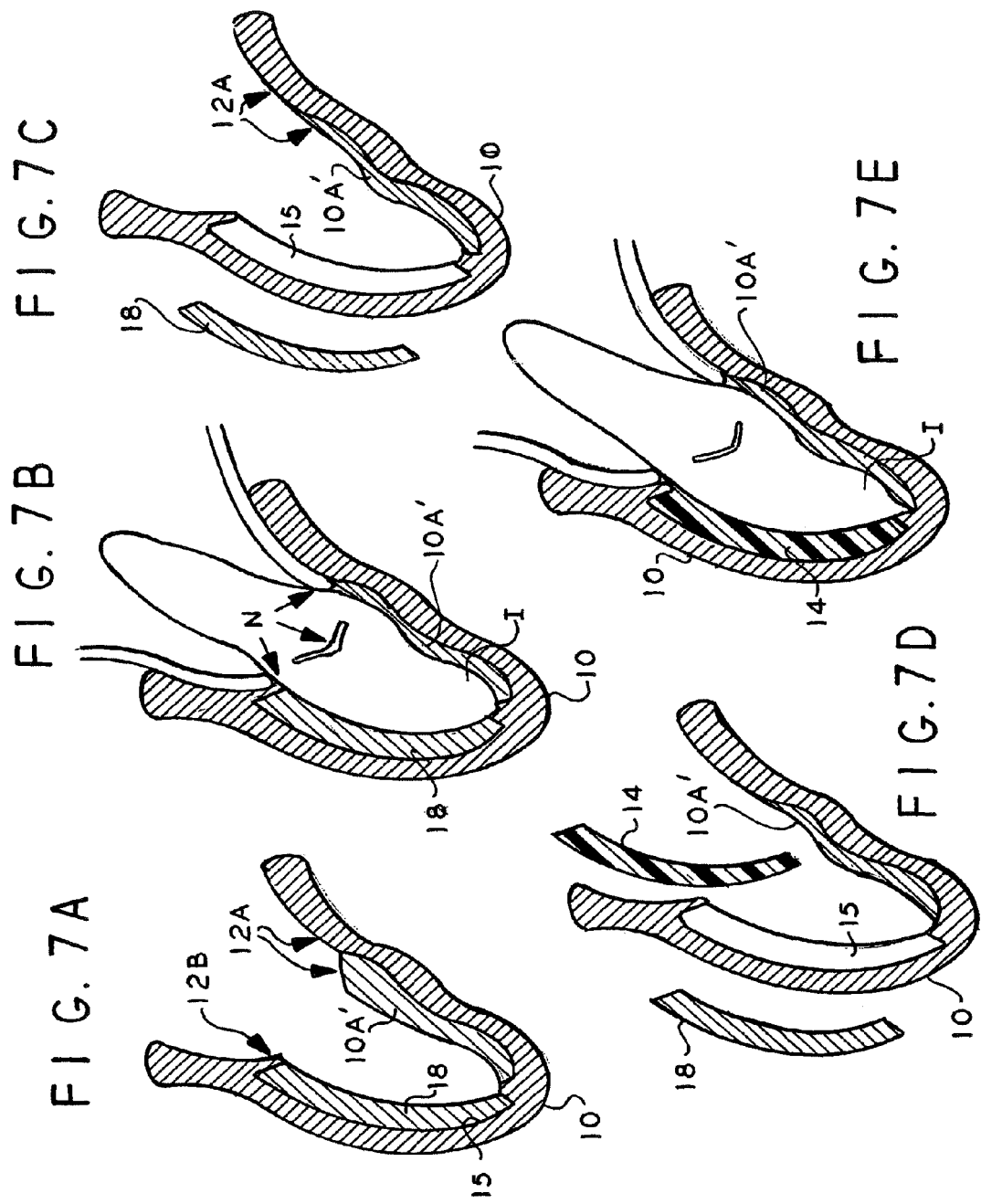

THERAPEUTIC AND PROTECTIVE DENTAL DEVICE USEFUL AS AN INTRA-ORAL DELIVERY SYSTEM

CROSS-REFERENCE TO RELATED APPLICATIONS

This application is a continuation of U.S. application Ser. No. 12/001,571, filed on Dec. 12, 2007, which is a divisional of U.S. application Ser. No. 10/138,821, filed May 6, 2002, the entire disclosures of which are hereby incorporated by reference.

BACKGROUND OF THE INVENTION

1. Field of the Invention

The present invention relates to dental devices that are worn on an arch of teeth, and in particular, to devices that can deliver a beneficial agent to, and protect the teeth and soft tissues from mechanical, chemical and biologic injury.

2. Description of Related Art

Mouthguards are typically made from plastics materials such as an ethylene vinyl acetate copolymer (EVA). Other devices such as dentoalveolar trays, carriers and splints may be made of EVA or other biocompatible plastic material. There are several categories of mouthguards: Mouthguards that are stock pre-molded products and made in a variety of sizes, home or self-moldable to suit the physical characteristics of the user, or custom molded by a dentist or other professional to suit the characteristics of the user. Regarding physical protection, stock mouthguards are typically the cheapest and least effective in use while the custom molded and shaped mouthguards are the most expensive and effective in their impact absorbent properties.

Athletes in many sports wear mouthguards for prolonged periods. It is common knowledge that when these athletes engage in strenuous physical activity, they lose and must replace significant amounts of fluids, nutrients and calories. In order to hydrate themselves, and replenish their energy, athletes must drink large quantities of fluids and eat foods that are very often cariogenic. These cariogenic fluids and materials cover the teeth, and when a mouthguard is inserted afterwards, the teeth are acted upon by cariogenic bacteria in an ideal environment, shielded from the buffering ability of saliva. In athletes, factors that serve to diminish salivary flow around the teeth include the general sympathetic tone of the nervous system, dehydration and shielding of the teeth by a mouthguard. Moreover, the elderly, patients suffering from a variety of autoimmune diseases, patients on a variety of medications and patients treated in the head region with external beam radiation may also suffer from reduced salivary flow. Whatever the cause, reduced salivary flow greatly increases the incidence of dental caries and periodontal disease.

U.S. Pat. No. 4,920,984 relates to a mouthguard material that may be custom shaped or molded employing a teeth impression cast pressed against softened thermoplastic sheet material that increases in thickness from one end to the other.

Australian patent specification 633269 discloses a mouthguard made from an EVA copolymer having a softening point higher than the normal temperature of an oral cavity but lower than the highest temperature that the oral cavity can endure so that the user may adapt the mouthguard to fit the mouth by biting onto it after it has been heated. The shaping procedure may be repeated if the shape or configuration of the teeth should change.

In FIG. 15 of U.S. Pat. No. 5,082,007 a gel or fluid capsule is contained between the upper and lower portions of a mouthguard. The nature of this gel is not described and appears to serve a mechanical, that is, a shock absorbing function.

It is not only known to employ materials enabling custom or self shaping of mouthguards, it has been suggested that mouthguards use other additives in the material of construction to enhance the characteristics of the material. For example, in U.S. Pat. No. 4,044,762 an athletic mouthguard is formed from a mixture of a plastic resin (e.g., an ethylene vinyl acetate that can be heated and softened to form a custom-fitted impression) and a fluoride compound that protects the wearer's teeth. As an alternative, the reference suggests spraying or otherwise coating the surface of a mouthguard with a fluoride compound. This fluoride compound is gradually delivered while the mouthguard is worn.

In FIGS. 7 and 8 of U.S. Pat. No. 5,323,787 a medicated pad is adhesively secured on the occlusal surface of a mouthpiece to treat the teeth and gums. The pad is saturated with a medicating substance in an intermediate layer of absorbent polymeric or fabric material, and that intermediate layer is overlaid with a non-porous outer layer. The pad can either be replaced or soaked to renew the medication. Specific medications are not discussed, although for other embodiments the mouthpiece is soaked in sterilizing (bactericides) and mouth-refreshing ingredients such as flavorings of the type used in conventional mouthwashes.

German patent specification 401 1204 discloses a mouthguard material consisting of an EVA copolymer material, polycaprolactone and colorants and perfumes and PVA (polyvinyl acetate) to reduce the softening point of the resultant mouthguard for ease of manipulation and shaping.

In U.S. Pat. No. 5,395,392 an infant's pacifier has a perforated mouth bulb containing an powder, syrup, or tablet with an agent such as monoclonal antibodies, fluorides, sorbitol, or xylite (xylitol).

Xylitol is a naturally occurring sugar. It is a five-carbon polyalcohol, pentitol, which is widely distributed in nature. Most fruits, berries and plants contain xylitol. Xylitol is also an intermediate of mammalian carbohydrate metabolism. Our bodies produce up to 1 5 grams of xylitol from other food sources using established energy pathways. Xylitol use is known to reduce tooth decay rates both in high-risk groups (high caries prevalence, poor nutrition, and poor oral hygiene) and in low risk groups (low caries incidence using all current prevention recommendations). Sugar-free chewing gums and candies made with xylitol as the principal sweetener have already received official endorsements from numerous international dental associations. Studies using xylitol as either a sugar substitute or a small dietary addition have demonstrated a dramatic reduction in new tooth decay, along with arrest and even some reversal of existing dental caries. Xylitol provides additional protection that enhances all existing prevention methods. This xylitol effect is long lasting and possibly permanent. Low decay rates persist even years after the trials have been completed.

For the anticariogenic activity of casein phosphopeptides, see U.S. Pat. No. 5,015,628; 5,834,427 (method of preparing casein phosphopeptides); and U.S Pat. No. 5,981,475. For various remineralizing compositions, see U.S. Pat. Nos. 4,348,381; 5,562,895; 5,895,641; and 6,036,944.

For various mouthguards and similar dental devices, see U.S. Pat. No. 4,554,154 (plastic that is chewable or usable as dental floss carries remineralizing, immunological, and antibacterial agents; e.g. sodium fluoride, chlorhexidine and lysozyme); U.S. Pat. No. 5,085,585 (U-shaped applicator is placed over teeth to apply medicaments to teeth and gum pockets); U.S. Pat. No. 5,194,003 (device that fits over teeth releases beneficial agents from a reservoir); U.S. Pat. No. 5,339,832 (composite mouthguard with integral shock-absorbing framework);U.S. Pat. No. 5,365,624 (mouthpieces with cleaning motors or gum cushioning material); and U.S. Pat. No. 6,012,919 (occlusal protector pad in an athlete's dental appliance has an upper layer of EVA and polycaprolactone).

Certain hydrogels, particularly synthetic hydrogels, can act as carriers for drugs and other active agents. These hydrogels allow passage of the agent, in some cases acting as a membrane that allows agent passage. Covalently crosslinked hydrogels can incorporate a drug or other agent during the polymerization step; or the agent can be loaded from a solution. These types of hydrogels tend, however, to be weak when swollen by its water content. With thermoplastic (solvent soluble) hydrogels, an agent or drug can be compounded with the polymer during extrusion or injection molding; or by combining the agent with the polymer solution in a suitable solvent. See "Hypan® Hydrogels" published by Hymedix International, Inc. The Hypan® hydrogels can be obtained with varying degrees of hydrophilicity. They can also be obtained either as relatively hard, crystalline blocks, used for structural applications; or as meltable transient clusters that are highly swelling, and useful as emulsifiers, gelling agents, and drug carriers. Various other suppliers of hydrogel exist as well.

For hydrogels with improved stability, see U.S. Pat. No. 5,346,935. See also U.S. Pat. No. 5,071,657 (transdermal administration of a medicinal agent dissolved in a nonflowable gel distributed in a microdisperse mode in a crosslinked silicone elastomer);U.S. Pat. No. 5,200,194 (oral osmotic device has a beneficial agent and hydrophilic support fibers inside a semi-permeable membrane); and U.S. Pat. No. 5,252,692 (hydrophilic acrylic copolymers).

See also, U.S. Pat. No. 3,996,934 (bandage using microcapsules to deliver a drug); U.S. Pat. No. 5,366,935; 5,286,490 (transdermal patch delivers fluoride medication to treat osteoporosis or periodontal disease); and U.S. Pat. No. 5,925,372 (transdermal delivery system for ethanol soluble drugs).

Thus, while prior art devices are capable of delivering an agent to surfaces within the oral cavity, they lack the ability to deliver agents to selected surfaces within the oral cavity, or to deliver one or more agents to different oral surfaces simultaneously. The present invention fulfills this long-felt need by being able to selectively deliver agents to specific oral surfaces, and to be able to deliver multiple agents to different surfaces using a single device, which device includes numerous insets for receiving agent-containing inserts therein. This agent delivery function can be performed either independently of, or in conjunction with, the protective functions of the present invention, which can also act as an athletic mouthguard. Further, the present invention provides a means to recharge the device with an agent once that agent has been depleted.

SUMMARY OF THE INVENTION

In accordance with the illustrative embodiments demonstrating features and advantages of the present invention, there is provided a dental device having a U-shaped carrier with at least one channel for embracing an arch of teeth. The carrier has at least one recessed inset in the at least one channel. The dental device also has at least one discrete insert carrying a beneficial agent. This insert is adapted to fit into the inset and release the agent gradually.

In accordance with another aspect of the invention, the foregoing dental device also includes at least one blank removably fitted into the at least one inset.

In accordance with yet another aspect of the invention, a dental device has a U-shaped carrier with at least one channel for embracing an arch of teeth. The carrier has at least one recessed inset in the at least one channel. Also included is at least one discrete insert adapted to fit into the inset. The insert has a different physical character (e.g., softer) than the carrier and is positioned and shaped to mechanically buffer teeth of the arch from mechanical shocks.

In accordance with still yet another aspect of the invention, a dental device that can mechanically buffer an arch of teeth from mechanical shocks has a U-shaped carrier with at least one channel for embracing the arch of teeth. Also included is a beneficial agent suffused through at least a portion of the carrier. The beneficial agent includes xylitol or sorbitol in one case, or a remineralizing agent in another case.

In accordance with a further aspect of the invention, a method is provided that employs at least one insert and a U-shaped carrier having at least one channel with at least one recessed inset containing a blank. The method includes the step of softening at least a portion of the carrier along the channel. Another step is pressing an arch of teeth into the channel to make an impression. The method also includes the step of removing the blank from the at least one inset. Also included is the step of installing the at least one insert into the at least one inset.

In accordance with yet a further aspect of the invention, a method employs (1) a plurality of inserts suffused with a beneficial agent and (2) a U shaped carrier having at least one channel with a plurality of recessed insets. The method includes the step of installing selected ones of the inserts into less than all of the insets to from a first installed insert pattern. Another step is removing at least some of the inserts from the carrier. The method also includes the step of installing at least one of the inserts to form a second installed insert pattern. Thus, different oral regions can be affected by different insert patterns.

In accordance with still yet a further aspect of the invention, a method employs a beneficial agent and an athletic mouthguard. The method includes the step of suffusing the beneficial agent into the mouthguard. Another step is wearing the mouthguard in an athletic event.

In accordance with still yet a further aspect of the invention, there is provided a kit for preparing a dental device. The kit includes a dental device with at least one channel for embracing an arch of teeth. The dental device has a carrier with at least one recessed inset in the at least one channel. Also included is at least one discrete insert adapted to carry a beneficial agent. The insert is adapted to fit into the inset and release the agent gradually. Also included is at least one beneficial agent for incorporation into the at least one discrete insert.

In accordance with still yet a further aspect of the invention, there is provided a dental device having a core inside a liquid-permeable shell. The shell has a shape suitable for chewing or teething. The core carries a beneficial agent and is adapted to release the agent gradually.

Methods and devices in accordance with the foregoing can chemically and physically protect a person's teeth and gingiva. An oral device ("mouth-guard/carrier") or method of the foregoing type can directly apply agents to the teeth and, in one embodiment, provide for the mechanical protection of the teeth from trauma as a mouthguard. This mouthguard/carrier preferably contains individual undercut insets adjacent to each tooth or groups of teeth into which will be placed therapeutic agents contained in, for example, a hydrogel vehicle as described hereinafter. The number of insets per tooth may vary, ranging from one to three (or more) to accommodate the lingual/palatal, buccal and occlusal surfaces. The agent included in a preferred embodiment is the naturally occurring sugar, xylitol, although other beneficial agents are contemplated as well; for example, remineralizing agents, moisturizing agents, desensitizing agents, flavoring agents, breath fresheners, chemical and biological indicators, nutraceuticals, antibiotics, probiotics, other medications and chemotherapeutics, etc.

Two generalized embodiments are described. In one embodiment, the device provides an intra-oral device that serves as an athletic mouthguard, provides a novel means of enhanced shock absorption, and contains insets for agent-containing inserts to be described hereinafter. In some embodiments disposable inserts, containing agents to be described presently, are constructed primarily of hydrogels. The inserts are placed into the device and release the intended agents directly onto the surface of the teeth and/or gingiva. The novel shock absorption characteristics of the device result from the unique mechanical force-distributive and dissipating properties of the (e.g., hydrogel) inserts that are placed in the anterior region (generally from canine to canine) which serves an additional function of providing a novel additive cushioning property against mechanical trauma.

In another embodiment, the steps include providing an intra-oral carrier made out of standard and typical dental appliance materials intended solely as a vehicle with insets for holding inserts that contain active agents to be described, and for positioning these proximate to the dentoalveolar tissues. The carrier in this other embodiment is not necessarily intended to provide mechanical protection for the teeth as in the other embodiment.

Thus the present specification discloses an intra oral device that may or may not have mechanically protective features (i.e. function as a mouthguard, depending on embodiment), may be applied to the maxillary or mandibular arch and will serve to deliver intra-orally, chemicals, therapeutics, medications, pharmaceuticals, nutraceuticals, etc. covered by this application; specifically xylitol and other agents disclosed herein as exemplar applications of the agent delivery features of the present invention.

In one embodiment, the carrier material, made of orally acceptable plastics material, has one or more insets arranged to maximize mechanical protection of the teeth and surface contact to facilitate agent delivery. To maintain the shape and retentive integrity of the insets, preferably, blanks will fill the insets and will require removal in order to insert the hydrogel inserts. These blanks will be particularly useful in a "boil and bite," self-molding carrier or mouthguard.

It is an object of one embodiment of the present invention to provide the ability to directly apply, in a timely fashion, agents to prevent and/or reverse the decalcification of teeth, that is potentiated by the use of a mouthguard, some transient physiologic states, as well as some medical conditions and/or procedures or medications of a person.

It is a further object of the invention to provide an improved material (preferably, hydrogel inserts) that in conjunction with typical EVA mouthguard materials, or the like, provides enhanced impact absorbent properties.

BRIEF DESCRIPTION OF THE DRAWINGS

The above brief description as well as other objects, features and advantages of the present invention will be more fully appreciated by reference to the following detailed description of presently preferred but nonetheless illustrative embodiments in accordance with the present invention when taken in conjunction with the accompanying drawings, wherein:

FIGS. 7A-7E are a cross-sectional views of the device of FIG. 1 showing a sequence of steps performed when using that device;

DETAILED DESCRIPTION OF THE PREFERRED EMBODIMENTS

Figure 1:
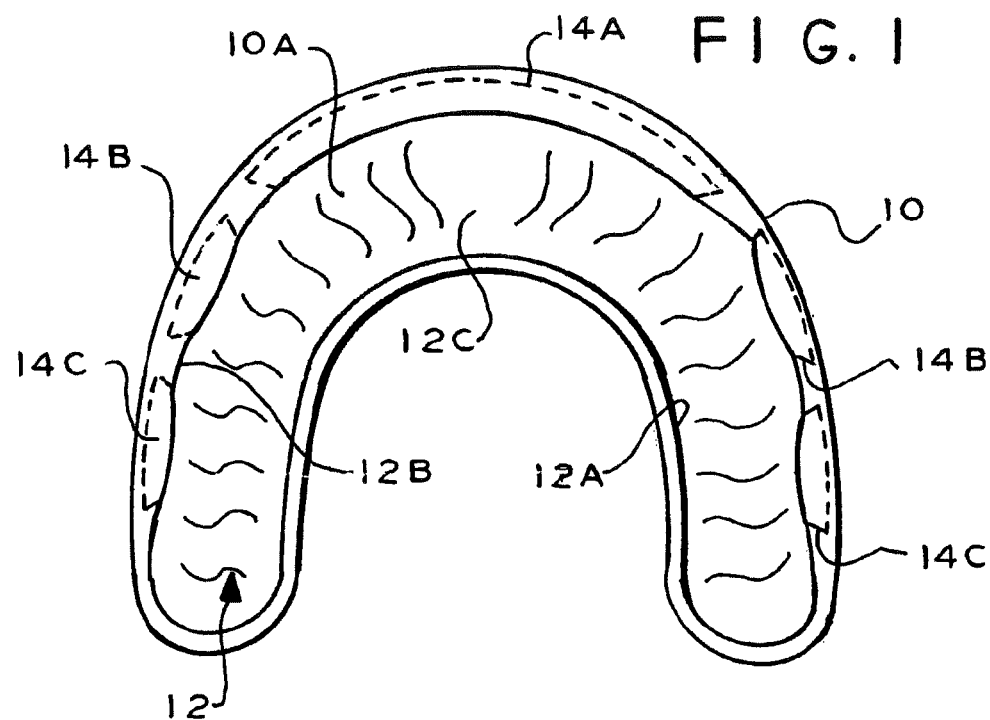
FIG. 1 is a plan view of a dental device showing the open channel of a U-shaped carrier.
Figure 2:
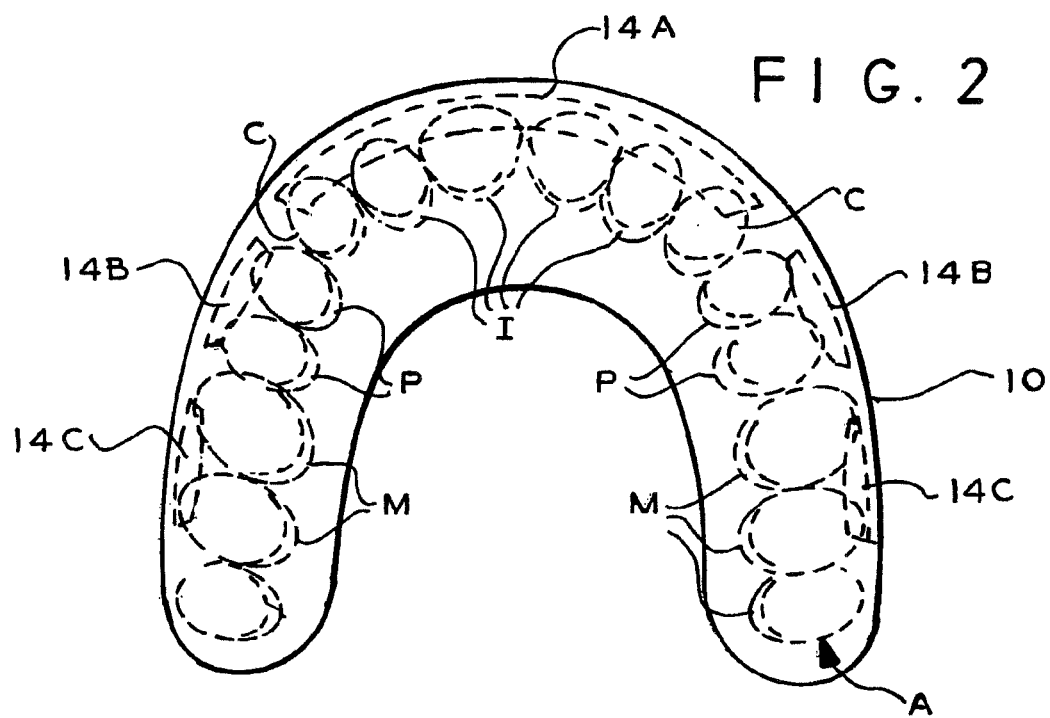
FIG. 2 is a plan view showing the reverse side of the dental device of FIG. 1.

Referring to FIGS. 1 and 2, a dental device is shown as a U-shaped carrier 10. Carrier 10 has a channel 12 serving as a recess for receiving an arch of teeth A. In this embodiment the device has only a single channel 12 for receiving the arch of teeth A, but other embodiments may have channels on opposite sides for receiving two arches of teeth. The inside wall 12A and outside wall 126 of channel are referred to as a lingual/palatal surface and buccal/labial surface, respectively. An occlusal/incisal surface 12C is located between surfaces 1 2A and 12B. Surfaces 1 2A-1 2C are collectively referred to as surfaces 12.

A central insert 1 4A is fitted into an inset in surface 1 2B, in front of four incisors I and two canines C of arch A (this combination being referred to as the anterior six teeth). A pair of back inserts 14B are also fitted into an inset in surface 1 2B, each in front of a pair of premolars P. Another pair of back inserts 1 4C are fitted into an inset in surface 1 2B, each in front of a pair of molars M (or in some cases all molars). Inserts 14A-14C are collectively referred to as inserts 14. These inserts 14 are placed symmetrically on the buccal surfaces.

The anterior insert 14A extends from canine to canine and laps the incisal edge and extends at least to the cervical junction. The two posterior inserts 146 and 14C are adjacent to the second premolar through the second molar teeth, extending at least to the cervical margins. This insert pattern is intended to act as mouthguard-carrier, but other patterns are contemplated, especially for embodiments that are primarily therapeutic.

As explained further hereinafter, a greater or lesser number of inserts may be employed, and these inserts can be designed to cover a greater or lesser number of teeth. Also, this dental device may be initially shipped without inserts, in which case plastic blanks will be initially installed in the insets normally containing inserts 14.

Preferably, and as described further hereinafter, hydrogel inserts will be emplaced within the buccal/labial wall 1 2B of the EVA plastic of carrier 10.

The intended material for carrier 10 may, for various embodiments, be any such material as is currently used in therapeutic dental carriers or sports mouthguards. Mouthguards are typically made from plastics materials such as an ethylene vinyl acetate copolymer (EVA). Additives may be added to the EVA itself to provide special properties for the mouthguard material. For example, a copolymer of ethylene and about 20% by weight vinyl acetate may be employed. In some embodiments of this device, flavoring and aromatic agents may be added to the polymer. Colorants, perfumes and softening agents may also be added as well.

There are generally three categories: (1) Mouthguards that are stock pre-molded products and made in a variety of sizes. (2) Home or self-moldable to suit the physical characteristics of the user. (3) Custom molded by a dentist or other professional to suit the characteristics of the user.

Typically, custom-made mouthguards are fabricated by a vacuum-forming or pressure-forming process whereby two or three laminar sheets of EVA are heat adapted to a mold. The number of lamina used and the thickness at any point will be determined by the intended use of the mouthguard/carrier, i.e. for therapeutics delivery only; or for delivery of therapeutics while worn as a protective mouthguard in sports related activities.

The illustrated embodiment is the self-moldable type. Accordingly, the occlusal/incisal surfaces 12C of the carrier 10 contain a chemically bonded low-temperature plastic layer 10A that deforms on heating to the temperature of boiling water (approximately 100 degrees Celsius). The user then "bites" into the channel 12 of device 10 and causes the low-temperature plastic component 10A to mold and conform to the user's dentoalveolar structures. The portion of the device 10 containing the insets intended to bear the hydrogel inserts 14A-14C is not permanently deformable. (Note relatively stiff blanks may be placed in the insets in the outer wall surface 12B of the EVA mouthguard/carrier 10 when an impression is made.)

In some embodiments, the carrier need not have separate inserts fitted into recessed insets, since the carrier itself can deliver a beneficial agent. The polymer may contain agents, such as xylitol. In some embodiments the polymer may contain a remineralizing agent for restoring calcium in teeth. Several flavors and/or aromas may be available to provide a wide selection to the user. The purpose of this beneficial agent and additives is to: (1) Provide an incentive for use of the mouth guard. (2) Alert the user when other beneficial agents are exhausted.

In some embodiments of the present invention, the carrier is not intended to provide mechanical protection as a mouthguard, but is intended solely as an agent delivery system and may be fabricated from orally acceptable plastics material and having multiple insets. In embodiments intended for primarily therapeutic application of active agents, there will be insets not only on the buccal/labial surface 1213, but on the lingual/palatal surface 12A as well (up to 32 for 16 teeth per arch, buccal and lingual surfaces). In any event the insets can receive hydrogel inserts for applying agents to the tissues in this vicinity.

Figure 3:
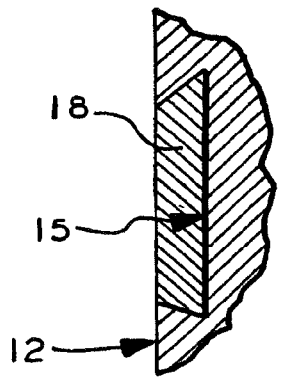
FIG. 3 is a detailed, cross-sectional view of a blank fitted into an undercut inset of the dental device of FIG. 1.

Referring to FIG. 3, during the manufacturing of the carrier 10, the shape and integrity of insets 15 are maintained by insert-shaped blanks 18 comprising the same material as the carrier 10. The blanks 18 would remain in place during any "boil and bite" type of customizing molding of stock mouthguard/carriers. The blanks 18 would be removed just prior to placement of the hydrogel inserts (see FIG. 4).

In the therapeutic carrier only embodiment, the blanks 18 may be left in place for certain sites where no therapy is intended. In this carrier embodiment, individualized insets 15 may be adjacent to each tooth or tooth region on the buccal and lingual surfaces for a maximum of 64 insets.

Figure 4:
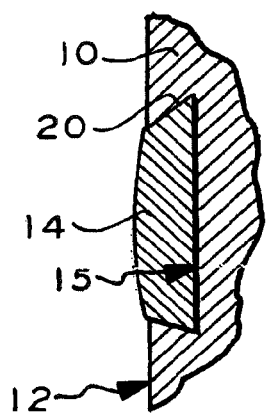
FIG. 4 is a detailed, cross-sectional view of an insert replacing the blank of FIG. 3.

Referring to FIG. 4, the innermost portion of previously mentioned surface 12, which is adjacent to the teeth and dentoalveolar tissues, will preferably hold preformed standard shaped inserts 14, formed of hydrogel vehicles suffused with intended beneficial agents. The walls of the insets 15 will be undercut to provide for a mechanical "snap-in" lock of the hydrogel material. Insert 14 is shown having a beveled edge 20 to accomplish this snap-in feature.

Figure 5:
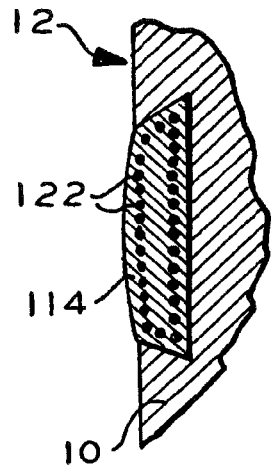
FIG. 5 is a detailed, cross-sectional view of an insert that is an alternate to that of FIG. 4.

Referring to FIG. 5, carrier 10 is shown fitted with an alternate insert 114. A matrix 122 embedded within insert 114 is in the form of a plastic mesh that enhances the rigidity and structural integrity of insert 114. Matrix 122 is shown spaced from the outer surfaces of inserts 114, but in some embodiments the mesh may be a porous covering encapsulating the hydrogel carrying the beneficial agent.

Figure 6A:
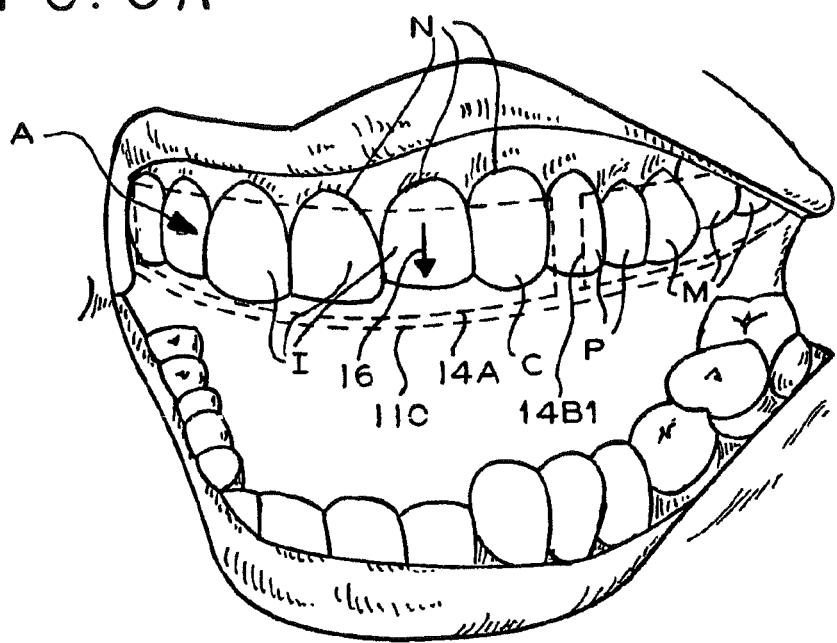
FIGS. 6A-6D are front views of dental arches showing in phantom four different arrangements of inserts for devices of the type shown in FIG. 1.

Referring to FIG. 6A, an upper arch A of teeth is shown overlaid in phantom with a carrier 110 similar to previously mentioned carrier 10. The teeth of arch A are marked as before. Again, center insert 14A is shown covering four incisors I and the canines C. In this embodiment, back insert 1481 has been lengthened from that of FIG. 2 to cover two premolars P and three molars M. This pattern and the pattern of FIG. 2 would be most appropriate for embodiments acting as a mouthguard that mechanically buffers teeth from mechanical shocks, although nothing would prevent these embodiments being used primarily for therapeutic purposes.

The cervical region of the teeth is that region where the teeth narrow down, or form a neck. This is normally found around cervical line N. In any event, the cervical region, as that term is used herein, is not intended to define a mathematically precise domain, but a region in the neighborhood of cervical line N. Directions extending away from the cervical region N across the crown of the teeth and toward the distal end of the teeth are indicated by direction arrow 16 and are referred to as a occlusal and incisal direction (or extending occlusally and incisally).

In this embodiment, the purpose of the device is twofold, i.e. to serve as a shock-absorbing mouthguard and therapeutic carrier. There are 3 (in some cases 5) insets in the buccal/labial wall of the mouthguard/carrier 110 into which is placed agent-containing hydrogels 14A and 14131. The hydrogels serve a second role of shock absorption and cushioning in order to protect the teeth from damaging physical contact.

Figure 6B:
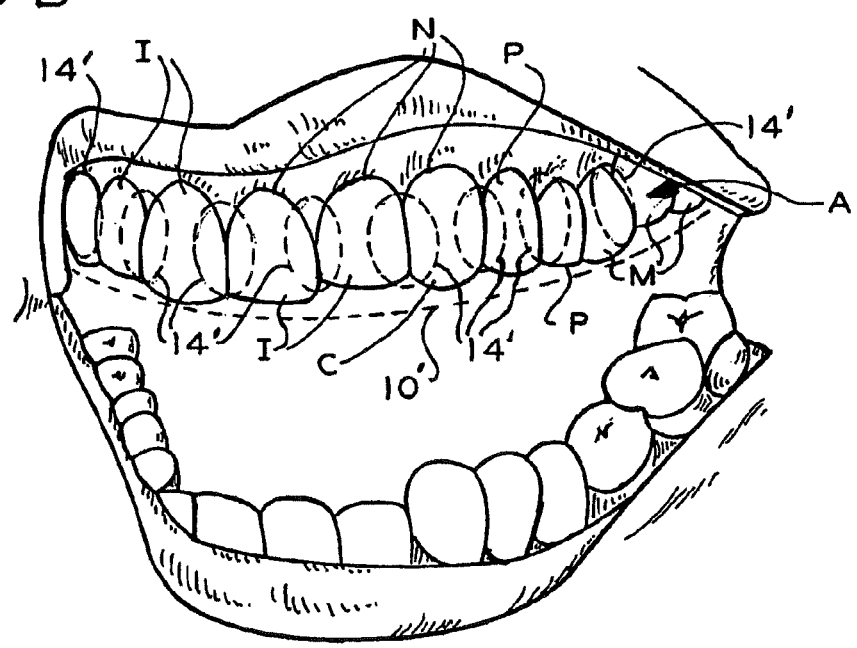

Referring to the embodiment of FIG. 6B, the purpose of the device is also twofold, i.e. to serve as a mouthguard, but primarily as a therapeutic carrier. There exist approximately 30 insets in the buccal/labial and lingual/palatal walls of the mouthguard/carrier into which are placed agent-containing inserts 14' made of hydrogels. The inserts 14' on opposite sides of the teeth will typically (but not necessarily) be in registry. The hydrogels will serve a second role of shock absorption and cushioning in order to protect the teeth from damaging physical contact, however, the primary role is to deliver agents to the teeth. The inserts 14' are each positioned to span across a pair of adjacent teeth. For strictly therapeutic purposes, not all of the inserts 14' will be installed but will be placed in a pattern appropriate for those teeth needing treatment.

Figure 6C:
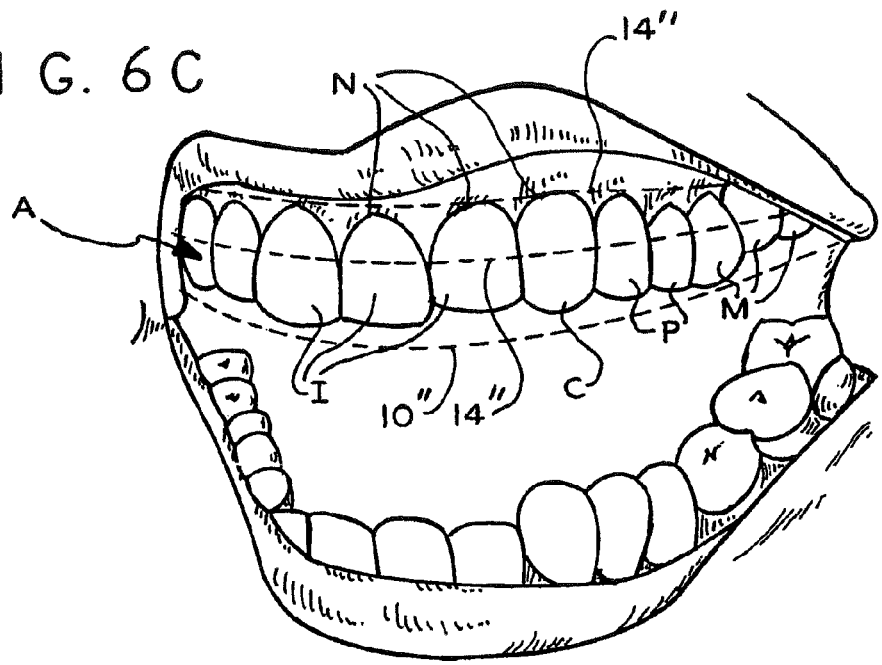

Referring to the embodiment of FIG. 6C, the purpose of the device 10" is as a therapeutic carrier to bring active agents to the periodontium, cervical areas and/or interproximal areas of the teeth. There exist one (up to three) insets located at the cervical margins N of the teeth on the buccal and lingual walls of the carrier 10" into which is placed agent-containing, hydrogel inserts 14".

Figure 6D:
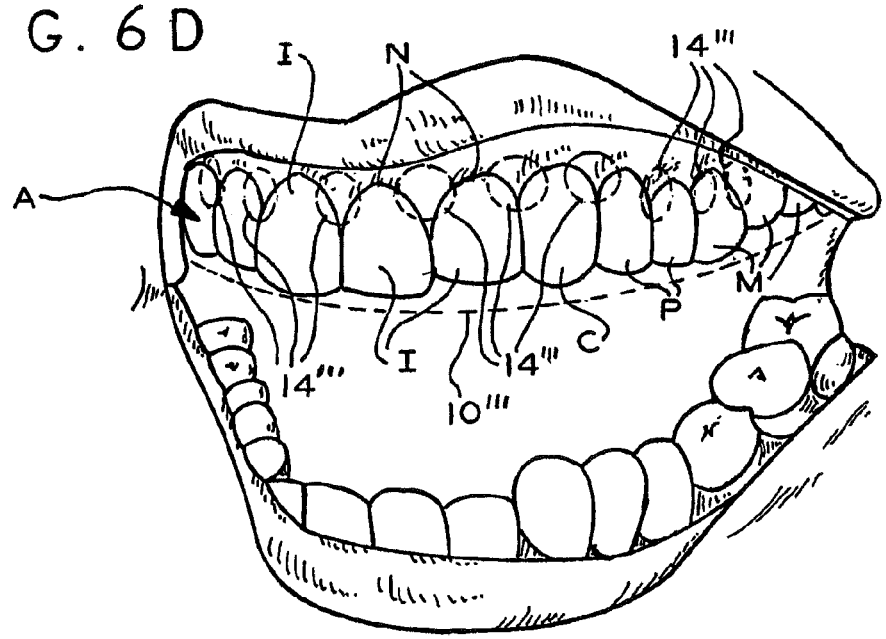

Referring to the embodiment of FIG. 6D, the purpose of the device 10''' is as a therapeutic carrier to bring active agents to the periodontium, cervical areas and/or interproximal areas of the teeth. There exist approximately 30 insets in the buccal/labial and lingual/palatal walls of the mouthguard/carrier into which are placed agent-containing hydrogels 14'''.

Referring to FIG. 7A, a cross-sectional view is given of mouthguard/carrier 10, through a location intended for a central incisor. The mouthguard 10 is in this embodiment a generic "stock" shape, composed of standard mouthguard material such as an ethylene vinyl acetate copolymer (EVA) substitute or equivalent.

In addition, there is an EVA blank 18 in the mouthguard/carrier's inset 15 intended to maintain the integrity of shape of the inset during a "boil and bite" heating process, to resist deformation. The boil and bite feature is provided herein by the moldable layer 1 OA' formed on surface 1 2A of carrier 10. Layer 10A' is chemically bonded to the EVA as a separate, low-temperature material attached to surfaces apart from the inset and strategically placed to conform to the dentoalveolar process and teeth of the user when the material is heated and the user "bites" into the mouthguard/carrier.

As shown in FIG. 7B, a user now "bites" into device 10 to make an impression on moldable layer 10A'. Significantly, blank 18 provides a firm surface for teeth such as incisor I, so that a reliable impression can be made.

Referring to FIG. 7C, after the molding process, the EVA blank 18 is removed, but moldable layer 10A' maintains an impression of the teeth. As shown in FIG. 7D, blank 18 will be replaced at an appropriate time with the agent-containing hydrogel insert 14.

Referring to FIG. 7E, in use, the hydrogel 14 is in contact with the labial surface of the incisor I, as well as other teeth. The hydrogel 14 releases, over time and in appropriate quantities, the active agent. In addition, the hydrogel's mechanical properties enhance the shock-absorbing properties of the carrier 10 as a mouthguard.

For embodiments having as their main purpose preventing and/or reversing cariogenic activity, inserts 14 will apply agents such as xylitol directly to the teeth. This beneficial agent allows the use of device 10 as a mouthguard, which would otherwise act to accelerate decalcification by shielding the teeth from the natural cleansing activity of the lips, cheeks and tongue and buffering action of the saliva. In addition, the vehicle intended to bring the active agents to the teeth (hydrogels 14) have unique physical properties that would be adjunctive in the dissipation of potentially harmful kinetic energy directed at the teeth. is that the hydrogel acts as a diffusion barrier that allows the agents to be released over a period of hours. Efficacious drug levels are achieved near the device surfaces, but the agents dilute out quickly into body fluids as they move away from the device. Only extremely low systemic levels of the agents result because of the dilution.

The preferred vehicle for agent delivery is a commercially available hydrogel, such as Hypan° hydrogel from Hymedix International, Inc., Dayton, N.J. This hydrogel is reported to be a hydrophilic acrylate derivative, with each polymer chain having several sequences of units with pendant hydrophilic groups (called soft blocks) and several sequences of pendant nitrile groups (referred to as hard blocks). The lengths of the blocks, and/or the nature of the side groups, as well as the overall hydrophilicity of the polymer, are varied depending upon production conditions.

Other hydrogels and agent-releasing vehicles from various sources and suppliers are contemplated for other embodiments. The preferred vehicles will be able to contain, and slowly release at a biocompatible rate and concentration, chemicals known to promote dental health and enamel and dentinal recalcification, such as: (1) Complex of calcium casein peptone derived from milk (CPP) and amorphous calcium phosphate (ACP), or CPP-ACP. (2) Xylitol. (3) Fluoride containing compounds, such as: (a) Sodium Fluoride; (b) Stannous Fluoride.

Other hydrogel materials which are contemplated by the present invention include compounds such as polyhydroxy ethyl methacrylate, chemically or physically crosslinked polyacrylamide, polyvinyl alcohols, poly(N-vinyl pyrolidone), polyethylene oxide, and hydrolyzed polyacrylonitrile. Polysaccharide-based hydrogels, such as covalent or chemically crosslinked polyvalent metal salts of alginates, pectines, carboxymethylcellulose, heparin and hyaluronic acid, as well as hydrogels containing chitin, chitosan, gellan, pullulan, and xanthan are also contemplated by the present invention.

Other fluoride containing compounds that may be suitable for use with the present invention include inorganic fluoride salts such as soluble alkali metals; alkaline earth metals; and heavy metal salts, for example, potassium fluoride, ammonium fluoride; cuprous fluoride; zinc fluoride; stannic fluoride; barium fluoride; sodium fluorosilicate; ammonium fluorosilicate; sodium fluorozirconate; aluminum mono- and difluorophosphate, fluorinated sodium calcium pyrophosphate and sodium monofluorophosphate. Calcium fluoride; cobalt ammonium fluoride; zinc ammonium fluoride; and stannous ammonium fluoride can also be used. Then known amine fluorides are also suitable organic fluorides which are contemplated by the present invention.

Also, the remineralizing or recalcifying agents envisioned herein may be various calcium salts such as calcium phosphate. A commercially available remineralizing agent is sold as Recaldent'''', although other remineralizing agents are contemplated. Other agents such as fluoride containing chemicals (e.g. stannous fluoride, sodium fluoride), xylitol may be used in combination. The chemical will be activated by saliva and released from the hydrogel material at a rate that will be non-toxic.

Examples of remineralizing agents include calcium compounds such as: amorphous calcium phosphate; amorphous calcium phosphate fluoride; amorphous calcium carbonate phosphate fluoride, amorphous calcium carbonate phosphate; potassium oxalate. Other compounds from which calcium ions may be obtained include calcium chlorides; calcium nitrate; calcium acetate; calcium benzoate; calcium butyrate; calcium gluconate; calcium formate; calcium fumarate; calcium glycerophophoshate; calcium lactate; calcium isobutyrate; calcium malate; calcium maleate; calcium proprionate and calcium valerate, and mixtures thereof.

Source of inorganic phosphorus for use in a remineralizing composition include mono- and dibasic calcium phosphate; dipotassium phosphate; monosodium phosphate; sodium metaphosphate; and alkali salts and ammonium salts of orthophosphoric acid, such as sodium, potassium or ammonium orthophosphate.

A water soluble salt, such as monobasic calcium orthophosphate, can also be used, as a source of both calcium and phosphate ions for use as a remineralizing agent.

The preferred vehicles will also be able to contain and gradually release agents suitable for treating periodontal disease, such as chlorhexidine, or various antibiotics. Chlorhexidine is most commonly used in the digluconate form, although other chlorhexidine containing compounds can be employed. Tetracycline, doxycycline, oxytetracycline, chloramphenicol, penicillin, amoxicillin, erythromycin, streptomycin, sulfonamides, aminoglycosides, cephalosporins, quinolones are among the antibiotics which can be employed in the present invention. Neomycin, kanamycin, amikacin, tobramycin and gentamycin are among the aminoglycoside antibiotics which can be used. Additional compounds can include antiviral agents, such as acyclovir or zidovudine; or antifungal agents, such as imidazoles or polyene antibiotics. Antibacterial agents such as benzethonium chloride, benzalkonium chloride, cetylpyridinium chloride, or dequalinium chloride are also contemplated. The preferred vehicles will also be able to appropriately deliver intraoral deodorants; and agents for improving the aesthetic appearance of teeth (whiteners), e.g., peroxide containing and peroxide generating compounds. It is also desirable to use a device that can flavor the carrier and therapeutic elements so as to provide an incentive to use the mouth guard, and alert the user that the protective elements are exhausted and may need to be replaced or recharged.

The present invention contemplates inclusion of sweeteners and flavorings known to those skilled in the art. These agents can be selected from among those in the following list, which is intended for examples only, and not intended as any limitation:

Sugar alcohols such as xylitol, sorbitol, mannitol, and mixtures thereof;

Water-soluble sweeteners, including monosaccharides, disaccharides and polysaccharides, such as xylose, ribose, glucose, mannose, galactose, fructose, sucrose, maltose, glycerine and partially hydrolyzed starch or corn syrup;

Artificial sweeteners such as aspartyl-phenylalanine methyl ester, acesulfame K, saccharin and sodium cyclamates.

As stated above, xylitol is a preferred sweetener because of its known non-cariogenic actions; sorbitol may also be substituted therefor.

The flavorings contemplated by the present invention include both natural and artificial flavors, and mint flavors such as spearmint and peppermint. Flavors such as wintergreen, anise and cinnamon are also included. Fruit flavors, including citrus flavors like orange, lemon and tangerine and other flavors, either individually or in blends thereof, are also included. These flavorings are generally utilized in concentrations that depend upon the individual flavor, and may range, for example only, in concentrations of approximately 0.05% to approximately 6% by weight of the final composition.

In addition, colorants may added to the compositions. Among the colorants are pigments which may comprise up to about 2% by weight of the composition. These colorants can include what are known to those skilled in the art as "FD & C" and "D&C" dyes, meaning dyes suitable for use in food, drug and cosmetic applications. It is preferred that the dyes utilized be watersoluble. Some examples include a triphenylmethane dye, FD&C Green #3, or a yellow dye designated D&C Yellow #10. The Kirk-Othmer Encyclopedia of Chemical Technology, $3^{rd}$ edition, volume 6, pages 361-495 contains a comprehensive listing of FD&C colorants which may be useful in conjunction with the present invention, including their chemical structures, and whose contents are hereby incorporated by reference herein.

In an embodiment of this device intended to serve as a mouthguard also, the hydrogel insert will be an integral component of the mouthguard and provide a mechanical barrier/cushion contributing to the cushioning and energy dissipative properties of the mouth guard. The hydrogel will have sufficient integrity of form to maintain its overall shape and to mechanically lock into the receptacle in the mouthguard. The integrity of form may be an intrinsic property of the hydrogel or may result from an encasement or framework that provides the necessary integrity of shape, yet allows an adequate diffusion of agent from the hydrogel. Indeed, the encasement may be desirable in order to control the rate of diffusion of the active agent.

In any event, following the instructions for use, the device and the hydrogel vehicle will deliver preferably not more than 15 grams of xylitol per 24 hours. At this rate of drug delivery, xylitol is fairly safe.

It is appreciated that various modifications may be implemented with respect to the above described, preferred embodiment. For example, the present invention may be distributed in the form of a kit, containing the dental device, one or more inserts, and a quantity of at least one beneficial agent which can then be incorporated into the insert of the dental device.

Figure 9:
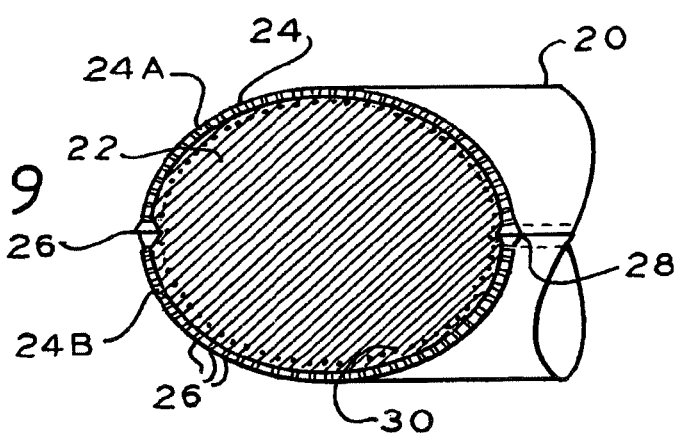
FIG. 9 is a cross-sectional view of the device of FIG. 9.
Figure 8:
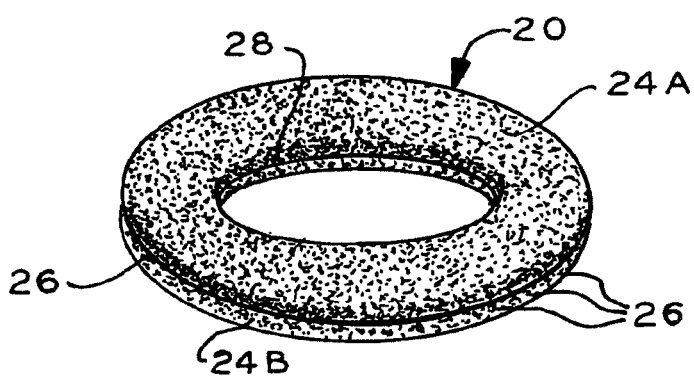
FIG. 8 is a perspective view of dental device that is an alternative to that of FIGS. 1-7 and is useful as a teething device for an infant.

Referring to FIGS. 8 and 9, the illustrated dental device 20 functions as an infant's teething device, although chewing by adult users are contemplated for some embodiments. While this device is shown as a ring or toroid, in other embodiments it may be shaped as a disk, a rod, or have various other shapes. In some embodiments the teething device may have a handle. In this embodiment the illustrated teething ring 20 has a toroidal core 22 made of a hydrogel as described above or a similar substance.

Core 22 may be contained inside a liquid-permeable shell, shown in this embodiment as a plastic skin 24 that is perforated by a multiplicity of orifices 26. These orifices may be arranged with a density of 10 to 1,000 orifices per square inch (1.6 to 160 orifices per square centimeter), although other embodiments may have a different density depending upon the desired permeability, skin strength, etc. The thickness of the skin 24 will vary with the strength of the skin's plastic material, balanced against the weakening effect of the orifices 26. The skin should be thick enough to avoid rupture, but thin enough to allow adequate diffusion of the active agents contained in the hydrogel core 22. For example, with a skin made of an EVA polymer, a skin thickness of 0.5 mm to 2.0 mm will operate satisfactorily, although in other embodiments the thickness may be outside this range. Furthermore, the distribution of orifices need not be uniform and may be more densely spaced in regions where the infant's gums or teeth engage the skin 24. The orifices 26 may be formed with a roller (not shown) having a large number of small piercing pins. The sheet of plastic skin, before installation, may pass over this roller, or the roller may be rolled over the plastic skin.

The skin 24 may be formed from an upper half 24A and a lower half 24B joined along an outer seam 26 and an inner seam 28. These seams may be welded by heat sealing, by gluing, or by other fastening means. Also, some embodiments may have just an inner seam 28, in which case the skin 24 will be one continuous piece with only one seam. Alternatively, the skin can be formed from more than two pieces. In some embodiments, the skin may be formed by spiral wrapping the skin around the toroidal shape. In still other embodiments, the skin may be molded in place either as a perforated surface or a continuous surface that is later perforated.

Core 22 is encased in an optional scrim 30, which will be a porous matrix such as a knit or woven fabric. Alternatively, scrim 30 may be a fibrous matrix that is readily penetrated by liquid, or a relatively impermeable sheet that is perforated by a number of holes to act as a permeable matrix.

In use, the infant may chew on the teething ring 20 in the usual fashion. The core 22 will be deformed and the active agent contained therein will tend to diffuse through the orifices 26. The core 22 can be suffused or impregnated with any one of the beneficial agents mentioned above, or any combination thereof. Also, in the instance of an infant's teething device, the beneficial agents may include substances appropriate for soothing the infant's gums. Such agents may be numbing agents or analgesics typically used to soothe the gums.

Obviously, many modifications and variations of the present invention are possible in light of the above teachings. It is therefore to be understood that within the scope of the appended claims, the invention may be practiced otherwise than as specifically described.

The invention claimed is:

1. An insert for a dental device, the dental device including a carrier having at least one channel adapted to receive at least a portion of an arch of teeth therein when the carrier is worn by a user, the carrier including at least one recessed inset defined by an inner surface extending into the carrier, the inset having an open end along a surface of the carrier, the insert comprising:
    a body discrete from the carrier having a predefined shape complementary to a shape of the inset such that the body is adapted to be detachably received within the inset in a received position in which an outer surface of the body is substantially contiguous with the inner surface of the inset.

2. The insert of claim 1, wherein, when the body is in the received position and the carrier is worn by the user, the body extends along the carrier so as to span a plurality of teeth of the arch and the body has an exposed surface along the open end of the inset, the exposed surface being substantially flush with the surface of the carrier adjacent to the inset.

3. The insert of claim 2, wherein the outer surface of the body is shaped to interact with the inner surface of the inset so as to form a snap-in lock that holds the body in the received position.

4. The insert of claim 3, wherein the body has a beveled edge shaped to engage an undercut of the inset so as to form the snap-in lock.

5. The insert of claim 2, wherein the body comprises pullulan.

6. The insert of claim 2, wherein the body is formed of a material having a beneficial agent suffused therethrough.

7. The insert of claim 1, wherein, when the body is in the received position and the carrier is worn by the user, the body extends along the carrier so as to span a plurality of teeth of the arch, and wherein the outer surface of the body is shaped to interact with the inner surface of the inset so as to form a snap-in lock that holds the body in the received position.

8. The insert of claim 7, wherein the body has a beveled edge shaped to engage an undercut of the inset so as to form the snap-in lock.

9. The insert of claim 7, wherein the body comprises pullulan.

10. The insert of claim 7, wherein the body is formed of a material having a beneficial agent suffused therethrough.

11. The insert of claim 1, wherein the body is formed of a material having a beneficial agent suffused therethrough, the body being shaped to interact with the inner surface of the inset so as to form a snap-in lock that holds the body in the received position.

12. The insert of claim 11, wherein the body has a beveled edge shaped to engage an undercut of the inset so as to form the snap-in lock.

13. The insert of claim 11, wherein the body comprises pullulan.

14. The insert of claim 11, wherein, when the body is in the received position, the body has an exposed surface along the open end of the inset, the exposed surface being substantially flush with the surface of the carrier adjacent to the inset.

15. A dental device, comprising:
    the insert of claim 1; and
    the carrier;
    wherein the channel of the carrier is bound by a buccal/labial wall, a lingual/palatal wall, and an occlusal/incisal wall therebetween, and wherein the inset of the carrier is located within either the buccal/labial wall or the lingual/palatal wall.

16. An insert for a dental device, the dental device including a carrier having at least one channel adapted to receive at least a portion of an arch of teeth therein when the carrier is worn by a user, the carrier including at least one recessed inset having an open end at a surface of the carrier, the insert comprising:
    a body discrete from the carrier, the body of the insert being adapted to be detachably received within the inset in a received position, wherein the body is shaped to interact with the inset so as to form a snap-in lock that holds the body in the received position.

17. The insert of claim 16, wherein, when the body is in the received position and the carrier is worn by the user, the body extends along the carrier so as to span a plurality of teeth of the arch.

18. The insert of claim 16, wherein the body of the insert is formed of a material having a beneficial agent suffused therethrough.

19. The insert of claim 16, wherein the body has a beveled edge shaped to engage an undercut of the inset so as to form the snap-in lock.

20. The insert of claim 16, wherein, when the body is in the received position, the body has an exposed surface along the open end of the inset, the exposed surface being substantially flush with the surface of the carrier adjacent to the inset.

21. The insert of claim 16, wherein the body comprises pullulan.

22. A dental device, comprising:
    the insert of claim 16; and
    the carrier;
    wherein the channel of the carrier is bound by a buccal/labial wall, a lingual/palatal wall, and an occlusal/incisal wall therebetween, and wherein the inset of the carrier is located within either the buccal/labial wall or the lingual/palatal wall.

23. A dental device, comprising:
    a carrier having at least one channel adapted to receive at least a portion of an arch of teeth therein when the carrier is worn by a user, the carrier including at least one recessed inset having an open end along a surface of the carrier; and
    at least one insert having a body discrete from the carrier, the body of the insert being adapted to be detachably received within the inset in a received position, wherein, when the body is in the received position, the body has an exposed surface along the open end of the inset, the exposed surface being substantially flush with the surface of the carrier adjacent to the inset.

24. The dental device of claim 23, wherein, when the body of the insert is in the received position and the carrier is worn by the user, the body and the inset extend along the carrier so as to span a plurality of teeth of the arch.

25. The dental device of claim 23, wherein the carrier is U-shaped so as to receive substantially the entire arch of teeth when the carrier is worn by the user.

* * * * *